United States Patent [19]
Hood

[11] Patent Number: 5,846,257
[45] Date of Patent: Dec. 8, 1998

[54] PRESSURE SENSOR FOR A SURGICAL SYSTEM

[75] Inventor: Larry L. Hood, Laguna Hills, Calif.

[73] Assignee: Nexus Medical System, Inc. LLC, Irvine, Calif.

[21] Appl. No.: 912,018

[22] Filed: Aug. 15, 1997

[51] Int. Cl.⁶ ..................................................... A61B 17/32
[52] U.S. Cl. ............................................. 606/167; 73/730
[58] Field of Search ..................................... 606/170, 171, 606/167; 73/730, 756, 861.42, 861.74, 861.75

[56] References Cited

U.S. PATENT DOCUMENTS 5,022,271   6/1991   Hannon, Jr. ................................. 73/730
5,024,099   6/1991   Lee ............................................. 73/730
5,630,826   5/1997   Sastri ........................................ 606/170

*Primary Examiner*—Michael Buiz
*Assistant Examiner*—Kevin Truong
*Attorney, Agent, or Firm*—Blakely, Sokoloff, Taylor & Zafman

[57] ABSTRACT

An apparatus that senses the pressure within a fluid line which has an external surface. The apparatus includes a sensor which has a probe that is in contact with the external surface of the fluid line. Any change in pressure deflects the fluid line and displaces the probe. The sensor provides an output signal that is representative of the probe displacement.

12 Claims, 2 Drawing Sheets

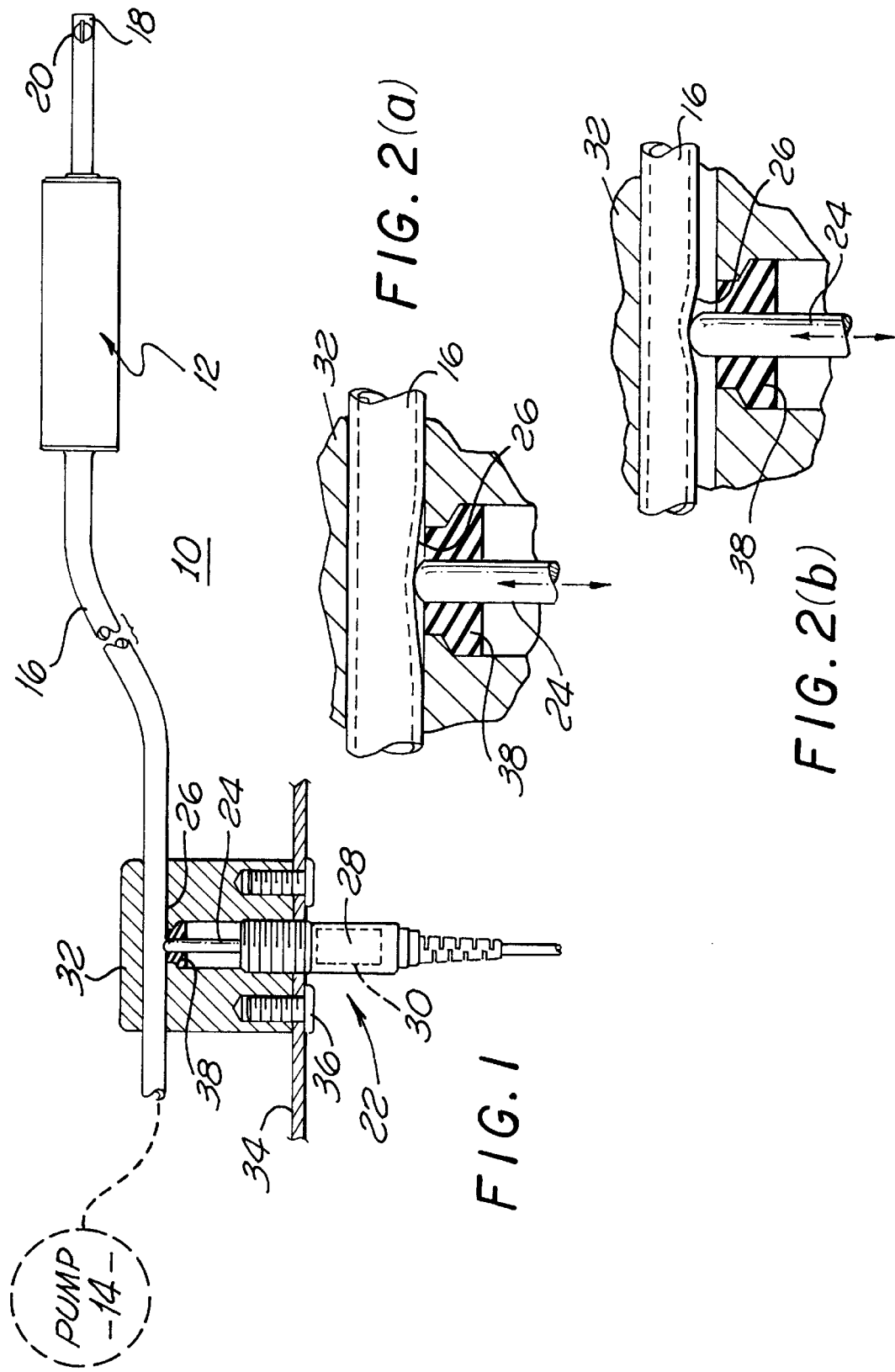

PRESSURE SENSOR FOR A SURGICAL SYSTEM

BACKGROUND OF THE INVENTION

1. Field of the Invention

The present invention relates to a pressure sensor that can sense the pressure of a fluid line without being in fluid communication with the line.

2. Background Information

There are various surgical procedures which utilize pneumatic vacuum/pressure systems. For example, the lens of a human eye is typically broken, removed and replaced in a procedure commonly referred to as phacoemulsification. Phaco procedures are typically performed with an ultrasonic cutter that breaks and emulsifies the lens. The cutter is coupled to an irrigation system which provides an irrigation fluid to the surgical site, and an aspiration system that aspirates both the irrigation fluid and the emulsified lens.

It is important to monitor the vacuum pressure of the irrigation system to insure that the fluid lines are not operating at an unsafe pressure level. For example, a piece of emulsified lens may occlude the irrigation line and restrict the flow of fluid through the line. The occlusion will also create a rapid reduction of pressure (increase in vacuum) on the upstream portion of the line. When the occlusion is dislodge there is a sudden surge of vacuum pressure that can collapse the cornea. Collapsing the cornea is an undesirable event which may result in permanent damage to the eye. For this reason many irrigation systems include a pressure sensor which can provide feedback on the fluid pressure within the irrigation line.

There have been developed various pressure sensors for ophthalmic systems. For example, there have been developed pressure transducers that can be inserted into the system. To insure sterility these types of transducers must be replaced after each procedure. Limiting the transducers to one use increases the cost of performing the procedures. Some irrigation systems utilize a plenum chamber which has a metal diaphragm and a capacitive/proximity sensor. Such transducers are relatively expensive.

It would be desirable to provide a pressure transducer that is inexpensive to produce and is not located in the sterile field so that the transducer does not have to be replaced after each surgical procedure.

SUMMARY OF THE INVENTION

An apparatus that senses the pressure within a fluid line which has an external surface. The apparatus includes a sensor which has a probe that is in contact with the external surface of the fluid line. Any change in pressure deflects the fluid line and displaces the probe. The sensor provides an output signal that is representative of the probe displacement.

BRIEF DESCRIPTION OF THE DRAWINGS

FIG. 1 is a schematic of a pressure sensor system of the present invention;

FIG. 2a is an enlarged view of a pressure sensor in contact with a fluid line;

FIG. 2b is a view similar to FIG. 2a showing the fluid line contracted and a sensor probe moved to a new position;

DETAILED DESCRIPTION OF THE INVENTION

Figure 3:
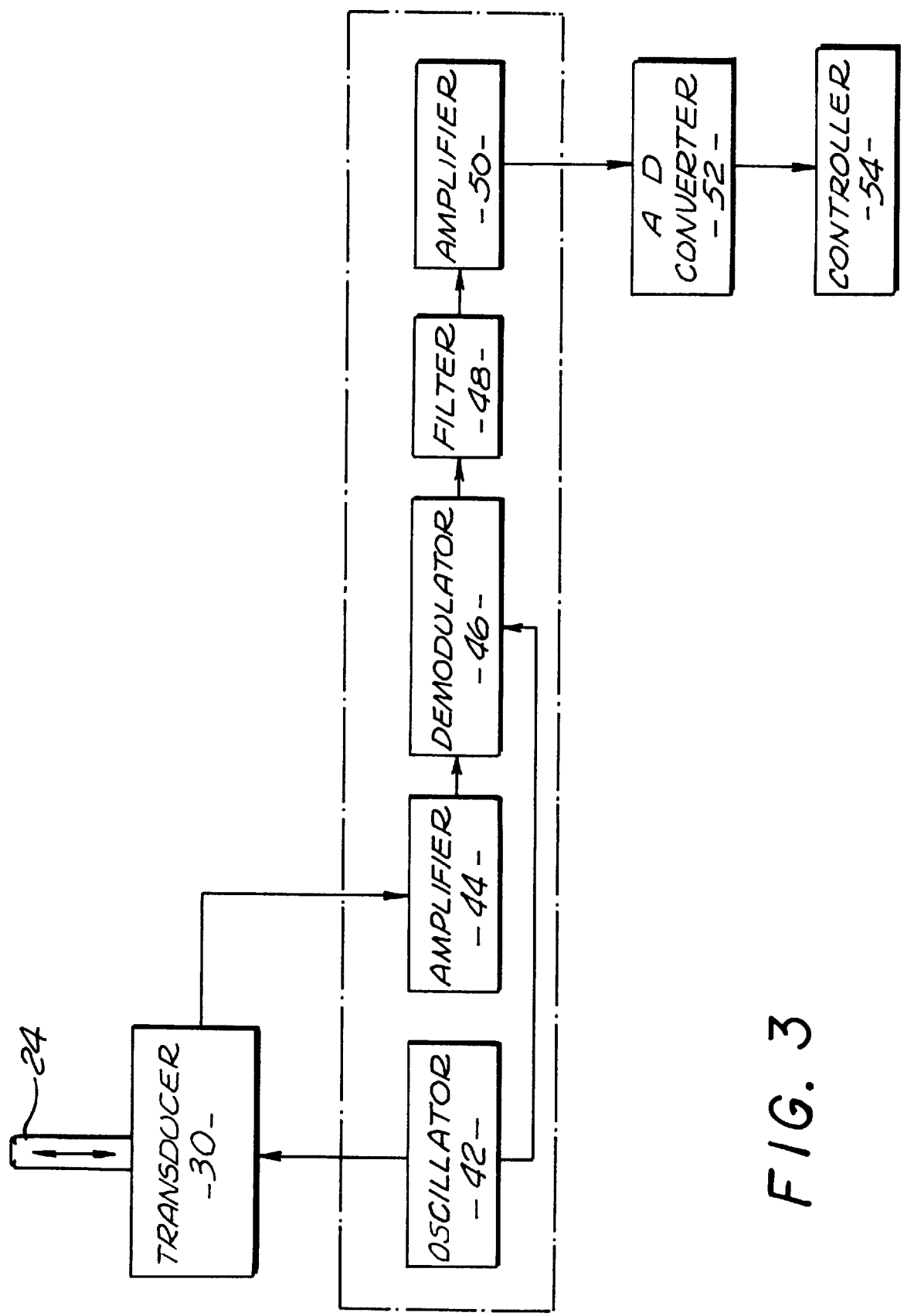
FIG. 3 is a schematic of a circuit for the system.

The present invention is an apparatus that is relatively inexpensive to produce and can sense the pressure within a fluid line without being in fluid communication with the fluid of the line. The apparatus includes a sensor which has a probe that is in contact with an external surface of the fluid line. A change in the line pressure will deflect the external surface of the fluid line. The deflection of the fluid line displaces the probe of the sensor. The sensor provides an output signal that is representative of the probe displacement. The output signal can be processed to determine the pressure level within the fluid line. When used in a surgical system the apparatus can thus monitor the pressure of a fluid line without being exposed to the sterile field. The use of the apparatus can be repeated without replacement or sterilization.

Referring to the drawings more particularly by reference numbers, FIG. 1 shows a surgical system 10. The system 10 is typically used to perform a medical procedure such as phacoemulsification, or a vitrectomy. The system 10 may include a cutter 12 that is coupled to a vacuum source 14 by a fluid line 16.

The cutter 12 may include an ultrasonically driven tip 18 that is inserted into the lens of a patient. An irrigation fluid is typically provided to the surgical site by an irrigation system (not shown). The vacuum source 14 may be a peristaltic pump or other device which creates a vacuum pressure within the fluid line 16 and at an aspiration port 20 of the cutter 12. The vacuum pressure pulls the irrigation fluid and any emulsified/cut tissue through the aspiration port 20 and the fluid line 16.

A sensor 22 is coupled to the fluid line 16 to measure the pressure within the line 16. The sensor 22 has a probe 24 that is contact with an external surface 26 of the fluid line 16. The fluid line 16 is typically constructed from a flexible material such as silicone rubber so that any change in the line pressure will deflect the external surface 26 of the line 16.

The probe 24 is displaced by any deflection of the external surface 26. For example, when the line pressure increases the external surface 26 will expand and the probe 24 will be displaced a distance which correlates to the amount of expansion. Likewise, when the line pressure decreases the external surface 26 will contract and the probe 24 will again be displaced a distance which correlates to the amount of contraction. The probe 24 may be spring loaded to move inward when the fluid line 16 contracts.

The probe 24 extends from a sensor housing 28 which contains a transducer 30 that provides an output signal. The output signal is representative of the probe displacement. By way of example, the transducer 30 may be a linear variable differential transducer ("LVDT"). The entire sensor 22 may be a LVDT device sold by Schaevitz under the product designation #LBB-375-TA-100. The Schaevitz device is spring loaded and provides ±0.100 inch of travel. Alternatively, the transducer 30 may be a linear optical encoder, or any other device which converts mechanical displacement to an electrical output signal.

The fluid line 16 and sensor 22 may be connected to a mounting block 32 that is mounted to a base plate 34 by fasteners 36. The sensor 22 may be have a rubber boot 38 to provide a seal with the block 32. The housing 28 of the sensor 22 can be screwed into the mounting block 32 so that the probe 24 deflects the fluid line 16 when the line is at an ambient pressure. By way of example, the probe 24 may provide an ambient deflection that is 10–50% of the inner diameter of the fluid line 16. The ambient deflection places the external surface 26 in tension so that there is relatively no lag between the change in line pressure and the deflection of the line 16.

FIGS. 2a and 2b show an operation of the sensor 22. The pressure of the fluid line 16 is reduced which contracts the external surface 26 of the fluid line 16. The contraction of the fluid line 16 causes the probe 24 to move in an inward direction. The transducer 30 provides an output signal which is representative of the probe displacement.

FIG. 3 shows a circuit 40 for processing the output signal of the sensor 22. The circuit 40 may include an oscillator 42 which generates a carrier signal that is provided to the transducer 30 of the sensor 22. Any movement of the probe 24 modulates the signal. The modulated output signal is provided to an amplifier 44. The amplifier 44 and oscillator 42 are connected to a demodulator circuit 46 which demodulates the output signal of the transducer 30. The demodulated output signal is filtered by filter 48, further amplified by amplifier 50 and provided to an analog to digital converter (A/D) 52 of a controller 54. The controller 54 contains a software algorithm(s) which can determine an exact pressure value within the fluid line from the demodulated output signal. The oscillator 42, amplifiers 44 and 50, demodulator 46 and filter 48 can be combined as a signal conditioner module 56 that is connected to an A/D converter port of a microprocessor.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. For example, although changes in vacuum pressure are shown and described, it is to be understood that the sensor 22 can also sense changes in positive pressure.

What is claimed is:

1. An apparatus that senses an internal line pressure of a fluid line which has an external surface and an inner diameter, comprising:

a sensor which has a probe that deflects the external surface of the fluid line between 10–50% of said inner diameter, and is displaced when the fluid line is further deflected by a change in the internal line pressure, said sensor provides an output signal that is representative of said probe displacement.

2. The apparatus as recited in claim 1, further comprising a housing which captures the fluid line and said sensor.

3. The apparatus as recited in claim 1, wherein said sensor is a linear variable differential transducer.

4. The apparatus as recited in claim 1, further comprising a signal conditioner module and a controller which process said output signal of said sensor to determine the pressure of the fluid line.

5. The apparatus as recited in claim 1, wherein said probe deflects the fluid line.

6. A surgical system, comprising:

a fluid line that has an external surface, an inner diameter and an internal line pressure;

a vacuum source that is coupled to said fluid line;

a cutter that is attached to said fluid line; and, a sensor which has a probe that deflects the external surface of the fluid line between 10–50% of said inner diameter, and is displaced when the fluid line is further deflected by a change in the internal line pressure, said sensor provides an output signal that is representative of said probe displacement.

7. The system as recited in claim 6, further comprising a housing which captures said fluid line and said sensor.

8. The system as recited in claim 6, wherein said sensor is a linear variable differential transducer.

9. The system as recited in claim 6, further comprising a signal conditioner module and a controller which process said output signal of said sensor to determine the internal line pressure of the fluid line.

10. The system as recited in claim 6, wherein said probe deflects said fluid line.

11. A method for sensing an internal line pressure of a fluid line which has an external surface, comprising:

a) deflecting the external surface between 10–50% of an inner diameter of the fluid line;

b) varying the internal line pressure of the fluid line, wherein the variation in pressure varies the deflection in the fluid line;

c) sensing the deflection in the fluid line; and, d) transmitting an output signal that is representative of the fluid line deflection.

12. The method as recited in claim 11, further comprising the step of determining the internal line pressure from the output signal.

* * * * *